United States Patent [19]

Smith

[11] 4,092,364

[45] May 30, 1978

[54] CAUSTIC HYDROLYSIS OF CHLOROBENZENE TO DIPHENYL OXIDE

[75] Inventor: William E. Smith, Midland, Mich.

[73] Assignee: The Dow Chemical Company, Midland, Mich.

[21] Appl. No.: 696,155

[22] Filed: Jun. 14, 1976

[51] Int. Cl.$^2$ ............................................. C07C 41/00
[52] U.S. Cl. ............................... 260/612 R; 568/747; 568/748
[58] Field of Search ........................... 260/612 R, 620

[56] References Cited

U.S. PATENT DOCUMENTS

| | | | |
|---|---|---|---|
| 1,744,961 | 1/1930 | Hale | 260/612 R |
| 1,972,605 | 9/1934 | Stoesser et al. | 260/612 R |
| 2,008,987 | 7/1935 | Marx et al. | 260/612 R |
| 2,079,383 | 5/1937 | Raeth et al. | 260/612 R X |
| 2,126,610 | 8/1938 | Britton | 260/612 R X |

*Primary Examiner*—Bernard Helfin
*Attorney, Agent, or Firm*—G. R. Plotecher

[57] ABSTRACT

The process of preparing diphenyl oxide from caustically hydrolyzing chlorobenzene, wherein phenol is a by-product, is improved by recycling the phenol. The improvement not only maximizes the yield of diphenyl oxide while minimizing the yield of phenol, but it also increases the yield of desirable by-products, such as phenylphenols and biphenylylphenyl ethers.

4 Claims, No Drawings

CAUSTIC HYDROLYSIS OF CHLOROBENZENE TO DIPHENYL OXIDE

BACKGROUND OF THE INVENTION

1. Field of the Invention

This invention relates to diphenyl oxide. In one aspect, this invention relates to a process of preparing diphenyl oxide from caustically hydrolyzing chlorobenzene. In another aspect, this invention relates to said caustic hydrolysis wherein phenol is a by-product.

2. Description of the Prior Art

Caustic hydrolysis of chlorobenzene is a process long known in the art for producing phenol and diphenyl oxide. Historically, phenol was the desired product and various methods of maximizing phenol yields were reported, such as recycling diphenyl oxide or adjusting the mole ratio of chlorobenzene to caustic. However, a number of different processes are available today for producing phenol, some economically more attractive than the caustic hydrolysis of chlorobenzene. Moreover, diphenyl oxide and other products from said caustic hydrolysis, such as phenylphenols and biphenylylphenyl ethers, have found commercial value. Consequently, phenol is no longer a necessarily desirable caustic hydrolysis product from chlorobenzene.

Where diphenyl oxide is the principally desired product, it is, of course, desirable to maximize its yield while minimizing the yield of phenol, preferably to a level where no net phenol (defined hereinafter) is produced. Heretofore reported caustic hydrolysis processes do not achieve this preferred objective.

SUMMARY OF THE INVENTION

According to this invention, the process of preparing diphenyl oxide from caustically hydrolyzing chlorobenzene wherein phenol is a by-product, is surprisingly improved by recycling the phenol. This improvement offers an effective method for maximizing the yield of diphenyl oxide while minimizing the yield of phenol. In fact, this improved process can be operated so that no net phenol is produced. Moreover, the yields of the phenylphenols and biphenylylphenyl ether by-products are increased.

DETAILED DESCRIPTION OF THE INVENTION

The caustic hydrolysis of chlorobenzene is typically conducted in a high-pressure autoclave at an elevated temperature, i.e., between about 350° C and about 450° C, and at a correspondingly high pressure. The vapor pressure of the reacting substances (aqueous caustic and chlorobenzene, the reaction mixture) is generally sufficient, but pressures in excess thereof are advantageous for convenient regulation and operation of the reaction, particularly where the autoclave is of the tubular type (which permits continuous operation). The reaction proceeds for about fifteen minutes and then the reaction products, in the form of an aqueous-organic biphasic mixture, are removed from the autoclave (continuously in the case of the tubular type of autoclave). Reaction products include diphenyl oxide, biphenylylphenyl ether isomers, phenylphenol isomers and phenol in the organic phase and sodium phenate and various phenylphenate isomers in the aqueous phase.

Where, as here, the desired product is diphenyl oxide, the two phases are usually physically separated. The organic phase is then washed with aqueous sodium hydroxide to remove the phenolics and subsequently distilled to recover the diphenyl oxide and the various biphenylylphenyl ether isomers. The aqueous caustic washings are combined with the separated aqueous phase and the resulting mixture is then neutralized with sufficient acid, such as hydrochloric acid, to free the phenolics from the corresponding phenates. Distillation of the neutralized mixture separates the phenylphenols (which are recovered) from the phenol. The phenol is then recycled to the high-pressure autoclave. Once recycle has been established, it is continuously operated and the amount of phenol in the reaction mixture is thus at all times maintained at the point where an approximate state of chemical balance with respect to such phenol exists. The formation of more phenol is thus markedly depressed.

Only the recycle of phenol is critical to this invention, the various above-described procedures being illustrative only. Thus such procedures can be modified to the individual needs of the practitioner without departing from the spirit of this invention. Moreover, the phenol can be recycled by any suitable means, this too being non-critical to the invention.

The expression "net phenol" as herein used is defined as the difference between the amount of phenol present in the reaction products, and the amount of phenol present in the reaction mixture at a given point in time. Consequently, where the amounts are the same, net phenol is zero. Where more phenol is present in the reaction products than in the reaction mixture, net phenol is a positive number (or the caustic hydrolysis of chlorobenzene is producing phenol). Where more phenol is present in the reaction mixture than the reaction products, net phenol is a negative number (or the caustic hydrolysis of chlorobenzene is consuming phenol). The present invention enables said caustic hydrolysis to operate at a net phenol of zero or less.

The amount of phenol recycled to the reaction mixture (recycled phenol) so that the net phenol is zero or less is dependent upon the caustic:chlorobenzene mole ratio. The larger the caustic:chlorobenzene mole ratio, generally the more recycled phenol required. For example, where said mole ratio is about 0.75:1, a phenol:chlorobenzene mole ratio of at least about 0.1:1 is employed. Where the caustic:chlorobenzene mole ratio is about 3.5:1, then a phenol:chlorobenzene mole ratio of at least about 2.5:1 is employed.

The minimum caustic:chlorobenzene mole ratio here used is generally about 0.75:1 and the maximum said ratio is generally about 3.5:1. The corresponding minimum phenol:chlorobenzene mole ratio here used (to achieve a net phenol of zero or less) is thus generally between about 0.1:1 and about 2.5:1. Practical considerations, such as convenience, equipment size and economy, are the only limitations on the maximum phenol:chlorobenzene mole ratio that can be used with a given caustic:chlorobenzene mole ratio. Although a low caustic:chlorobenzene mole ratio favors diphenyl oxide, phenylphenol and biphenylylphenyl ether production and disfavors phenol production, adjustment of the mole ratio without the presence of recycled phenol will not of itself result in net phenol of zero or less.

The following examples are illustrative of certain specific embodiments of this invention. However, these examples are for illustrative purposes only and should not be construed as limitations upon the invention.

SPECIFIC EMBODIMENTS

Control

Chlorobenzene (38.0 g, 0.68 mole) and a 15.4 percent aqueous solution of sodium hydroxide were charged to a 300-ml 3.5 percent nickel-steel high-pressure reactor equipped with a thermocouple well and sealing cap. The reactor was placed in an agitation rack and then heated to and maintained at 400° C ±5° C for about 12 minutes. The heat source was subsequently removed and the reactor cooled by water spray. The reactor contents were removed, separated, and then analyzed by gas liquid chromatography. The results are recorded in Table I.

EXAMPLES 1-6

Except for modifications in the caustic:chlorobenzene mole ratio and the addition of phenol to the reaction mixture, the control procedure was sextuplicated. The results of each repetition are also recorded in Table I.

TABLE I

COMPARATIVE DATA ON THE CAUSTIC HYDROLYSIS OF CHLOROBENZENE TO DIPHENYL OXIDE

| Example | MOLE RATIO | | Conv.[4] Cl$\phi$ % | YIELD | | | |
|---|---|---|---|---|---|---|---|
| | NaOH[1]/ Cl$\phi$[2] | $\phi$OH[3]/ Cl$\phi$ | | g $\phi$OH[3] 100 g Conv. Cl$\phi$ | g DPO[5] 100 g Conv. Cl$\phi$ | g $\phi\phi$OH[6] 100 g Conv. Cl$\phi$ | g $\phi\phi$O$\phi$[7] 100 g Conv. Cl$\phi$ |
| Control | 2.0 | 0 | 100.0 | 61.9 | 9.5 | 6.6 | 0.7 |
| 1 | 2.07 | 0.5 | 100.0 | 30.7 | 27.0 | 9.7 | 1.7 |
| 2 | 2.0 | 2.6 | 90.2 | −51.7 | 117.2 | 20.4 | 4.8 |
| 3 | 3.0 | 2.6 | 99.2 | −17.1 | 57.8 | 18.0 | 3.0 |
| 4 | 1.0 | 0.2 | 79.1 | 14.4 | 51.9 | 10.2 | 5.0 |
| 5 | 1.0 | 0.4 | 78.7 | −1.3 | 56.7 | 10.9 | 4.5 |
| 6 | 1.0 | 1.0 | 67.7 | −29.9 | 85.8 | 10.8 | 7.5 |

[1]Sodium hydroxide (caustic)
[2]Chlorobenzene
[3]Phenol
[4]Conversion
[5]Diphenyl oxide
[6]Phenylphenol
[7]Biphenylyl phenyl ether The control demonstrates a positive net phenol from the known caustic hydrolysis of chlorobenzene. Example 1 demonstrates that a phenol:chlorobenzene mole ratio of 0.5 is insufficient to achieve a net phenol of zero or less when the caustic:chlorobenzene mole ratio is 2, as does Example 4 where the phenol:chlorobenzene mole ratio is 0.2 and the caustic:chlorobenzene mole ratio is 1.0. However, Examples 2, 3, 5 and 6 clearly demonstrate that the presence of phenol in the reaction mixture at the stated mole ratios achieves a net phenol of zero or less. The negative numbers are indicative of this, i.e., more phenol was consumed than produced. Specifically, Example 2 states that for every 100 grams of chlorobenzene converted, 51.7 grams of phenol were consumed. Of course, the diphenyl oxide yields as well as the phenylphenol and biphenylyl phenyl ether yields were correspondingly increased.

What is claimed is:

1. In the noncatalytic process of preparing diphenyl oxide, biphenylylphenyl ethers and phenylphenols from caustically hydrolyzing chlorobenzene at a temperature between about 350° C and about 450° C and at high pressure wherein phenol is a by-product, the caustic and chlorobenzene present at a caustic:chlorobenzene mole ratio between about 0.75:1 and about 3.5:1 the improvement comprising: recycling the phenol such that the phenol and chlorobenzene are present at a phenol:chlorobenzene mole ratio between about 0.1:1 and about 2.5:1 and that a net phenol of zero or less is achieved.

2. The process of claim 1 wherein the chlorobenzene is caustically hydrolyzed at a temperature between about 350° C and about 450° C and at a corresponding vapor pressure.

3. The process of claim 1 wherein the caustic and chlorobenzene are present at a caustic:chlorobenzene mole ratio between about 1:1 and about 3:1.

4. The process of claim 3 wherein the phenol and chlorobenzene are present at a phenol:chlorobenzene mole ratio between about 0.3:1 and about 2:1.

* * * * *